United States Patent
Harttig

(10) Patent No.: US 8,608,669 B2
(45) Date of Patent: Dec. 17, 2013

(54) LANCET HAVING CAPILLARY CHANNEL AND STERILE PROTECTION ELEMENT AND METHOD FOR PRODUCING SUCH A LANCET

(75) Inventor: Herbert Harttig, Neustadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/187,623

(22) Filed: Jul. 21, 2011

(65) Prior Publication Data

US 2012/0022345 A1    Jan. 26, 2012

Related U.S. Application Data

(63) Continuation of application No. PCT/EP2009/009297, filed on Dec. 29, 2009.

(30) Foreign Application Priority Data

Jan. 21, 2009  (EP) .................................. 09000748

(51) Int. Cl.
- A61B 5/00   (2006.01)
- B65D 81/00  (2006.01)
- A61B 17/14  (2006.01)
- A61B 17/32  (2006.01)

(52) U.S. Cl.
USPC .............................. 600/583; 600/584; 606/181

(58) Field of Classification Search
USPC .................. 600/573, 583, 584; 606/181–183
See application file for complete search history.

(56) References Cited

U.S. PATENT DOCUMENTS

| | | | |
|---|---|---|---|
| 2003/0050573 A1 | 3/2003 | Kuhr et al. | |
| 2004/0236251 A1* | 11/2004 | Roe et al. | 600/583 |
| 2005/0036909 A1* | 2/2005 | Erickson et al. | 422/61 |
| 2005/0245954 A1 | 11/2005 | Roe et al. | |
| 2006/0079810 A1 | 4/2006 | Patel et al. | |
| 2007/0173740 A1 | 7/2007 | Chan et al. | |
| 2007/0197937 A1 | 8/2007 | Sarofim et al. | |
| 2008/0040919 A1 | 2/2008 | Griss et al. | |
| 2008/0103415 A1 | 5/2008 | Roe et al. | |
| 2009/0010802 A1* | 1/2009 | Joseph et al. | 422/22 |
| 2009/0287116 A1 | 11/2009 | Konya | |
| 2010/0044260 A1 | 2/2010 | Niederberger et al. | |

FOREIGN PATENT DOCUMENTS

| | | | |
|---|---|---|---|
| EP | 1360935 A1 | 11/2003 | |
| EP | 1894525 A1 | 3/2008 | |
| EP | 1961381 A1 | 8/2008 | |
| WO | 2004075760 A1 | 9/2004 | |
| WO | 2005104948 A1 | 11/2005 | |

* cited by examiner

Primary Examiner — Brian Szmal
Assistant Examiner — Megan Leedy
(74) Attorney, Agent, or Firm — Harness, Dickey

(57) ABSTRACT

Lancets comprising a piercing element for puncturing the skin of a patient, a test region containing detection reagents for determining an analyte concentration of a body fluid sample, a capillary structure arranged in the piercing element for transporting a body fluid sample to the test region, and a sterile protection element, which encloses the tip of the piercing element. The capillary structure is blocked in a section surrounded by the sterile protection element. Also provided are methods for producing a lancet, comprising: producing a piercing element, which on the upper side has an upwardly open capillary structure; covering a section of the upper side of the piercing element and blocking the capillary channel in this section using a first material; covering a section of the underside using a second material; sterilizing the piercing element; and attaching a test region containing detection reagents to the piercing element.

13 Claims, 2 Drawing Sheets

LANCET HAVING CAPILLARY CHANNEL AND STERILE PROTECTION ELEMENT AND METHOD FOR PRODUCING SUCH A LANCET

CROSS-REFERENCE TO RELATED APPLICATIONS

This application is a continuation of International Patent Application No. PCT/EP2009/009297, filed Dec. 29, 2009, which claims the benefit and priority of European Patent Application No. 09000748.5, filed Jan. 21, 2009. The entire disclosures of the above applications are incorporated herein by reference.

BACKGROUND

The invention relates to lancets for determining the concentration of an analyte concentration in a body fluid sample. The invention further relates to methods for producing such a lancet having a sterile protection element.

Lancets are known which comprise integrated test regions that contain detection reagents for determining an analyte concentration, for example the glucose concentration. See, European Patent Application Publication No. EP 1360935 A1, Olson et al., published Nov. 12, 2003. The lancets are individually sealed in chambers of a carrier strip and thereby protected from harmful influences of the environment. However, sterilizing the lancets has the risk of impairing the test regions.

It is therefore the object of the invention to cost-effectively produce and store lancets that have a test region containing detection reagents and a capillary structure for transporting a body fluid sample to the test region.

SUMMARY

According to the invention, the capillary structure is blocked in a region surrounded by the sterile protection element, preferably in that the sterile protection element fills in the capillary structure at least over a part of the length.

Advantageously, in order to produce a lancet according to the invention, first the tip of the piercing element can be enclosed in the sterile protection element so that, after sterilization, the piercing element can be handled without any problems without the risk of contamination. In particular, later a test region can be attached without difficulty to the sterilized piercing element, for example by fastening a test region carrier to the piercing element. With such a procedure, the sterilization process does not impair sensitive detection reagents of the test region. Complex covering of the test region during sterilization of the lancet due to the effect of radiation is then not required, even when using detection reagents that are sensitive to radiation, because the test region is not attached to the piercing element until after sterilization and is thus located on a part of the lancet that protrudes from the sterile protection element.

Advantageously, in a lancet according to the invention the tip of the piercing element and the part of the capillary structure entering the body of a patient during a puncture can be kept functional, clean and sterile, even with extremely long storage. Since the capillary structure is blocked, it is excluded in a lancet according to the invention that material can travel from the test region via the capillary structure into a front part of the lancet and, during puncture, into the body of a patient. When simply sealing a lancet in a chamber, as is described in EP 1360935 A1, however, there is the risk that over time enzymes or dust migrate into the capillary structure and cause a hydrophobizing effect, or even travel into the body the patient during puncture and cause damage there.

The piercing element is preferably not sterilized until after the sterile protection element has been attached, preferably by the effect of radiation, for example electron or gamma radiation. However, in principle it is also possible to sterilize the piercing element first and then attach the sterile protection element. The corresponding steps of the method as set forth herein (i.e., covering the upper side of the piercing element, covering the underside of the piercing element, and sterilizing) can be carried out in any arbitrary sequence. The sequence of listing of the steps as set forth herein does not mean that the steps must be carried out in this sequence.

A lancet according to the invention is preferably arranged on a carrier strip. It is particularly preferred to seal the individual lancets with the sterile protection element in chambers. Suitable chambers can be easily produced by a carrier strip and a film covering each lancet.

The sterile protection element of a lancet according to the invention is preferably composed of at least two components. To this end, a first component covers a section of an upper side of the piercing element and fills in the capillary structure in the covered section. The first component is preferably a film. A second component covers a section of an underside of the piercing element, so that the tip thereof is enclosed. The second component is preferably a film. The upper side and underside shall be regarded as two opposing regions of the piercing element that extend in the longitudinal direction thereof. For example, the piercing element can have an approximately cylindrical shape, so that the upper side and the underside each have an approximately semicircular cross-section. The piercing element, however, is preferably flat, for example cut out of sheet metal.

The capillary structure can be potted with a first component, for example. However, the first component is preferably pressed into the capillary structure, because then the first component can be removed more easily again from the capillary structure. It is particularly preferred if the first component is plastically deformed when pressed in. The piercing element can, for example, be placed between two films, which are then pressed together, so that one of the two films deforms as the first component and is pressed into the capillary structure. The two films are then bonded and can be glued or welded together, for example. The first film is preferably thicker than the second film, preferably at least five times as thick, and more particularly at least ten times as thick. It is particularly preferred if the thickness of the first film is greater than the depth of the capillary structure, and more particularly at least 10% greater. It is particularly preferred if the second film is thinner than the piercing element and has a thickness of, for example, no more than 20% the thickness of the piercing element.

The first component is preferably a polymer material. However, it is also possible to use metallic materials, for example metal foams or fibrous materials.

The first component is preferably porous, for example a foamed material, notably a polymer foam. This measure has the advantage that the first component can be pressed particularly well into the capillary structure and removed therefrom.

The capillary structure of a lancet according to the invention is preferably a capillary channel. The capillary channel is preferably designed as a groove. However, it is also possible for the capillary channel to be a continuous slot, so that the capillary channel is open toward both the upper side and the underside of the piercing element. The capillary structure is preferably hydrophilized, for example by a plasma treatment or by being provided with a hydrophilic coating, for example made of heparin.

DRAWINGS

Further details and advantages of the invention will be described based on an embodiment with reference to the attached drawings.

Figure 2:
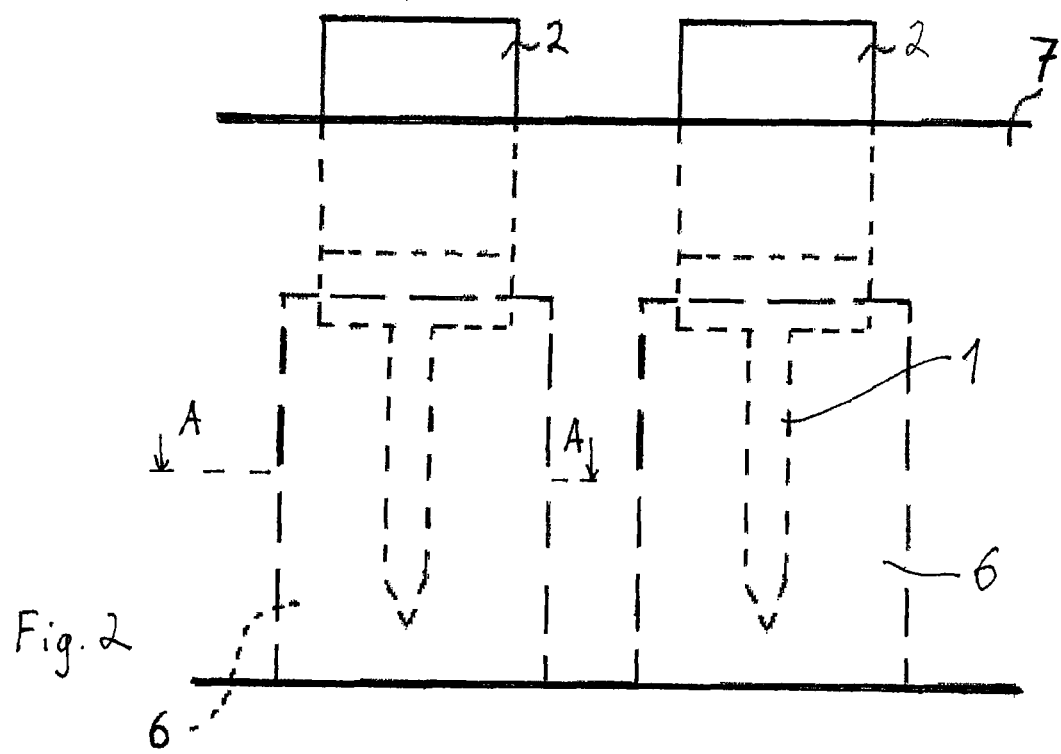
FIG. 2 shows such lances having a sterile protection element on a carrier strip.
Figure 4:
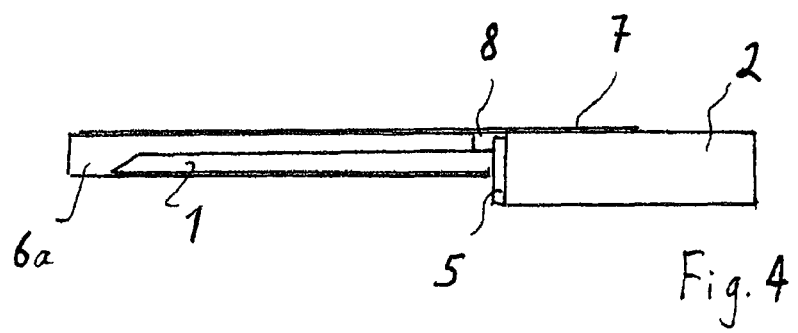
Figure 5:
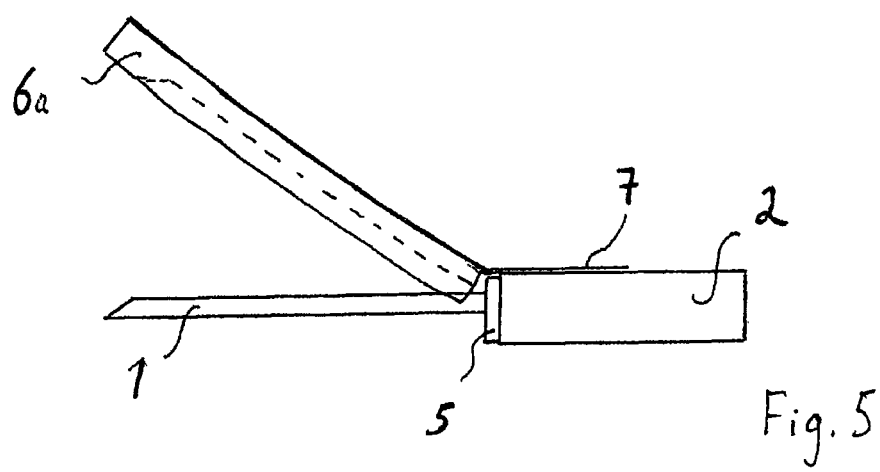

FIG. 4 a side view of FIG. 2;

FIG. 5 shows the removal of the sterile protection element.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
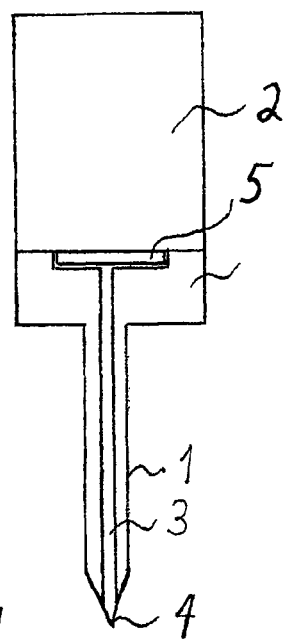
FIG. 1 is an embodiment of a lancet according to the invention without sterile protection element.

The lancet shown schematically in FIG. 1 comprises a piercing element 1 and a carrier body 2. The piercing element 1 is preferably made of metal, and more particularly steel, and can be cut, for example, out of sheet metal, for example by stamping, etching or laser cutting. However, the piercing element 1 can also be produced from a ceramic material or synthetic material. A suitable piercing element can be produced, for example, in the manner described in International Publication No. WO 2006/066744 A1, Griss et al., published Jun. 29, 2006 (see also U.S. Patent Application Publication No. US2008/0040919, Griss et al., published Feb. 21, 2008).

In the piercing element 1, a capillary channel 3 is arranged as the capillary structure, which in the embodiment shown extends from the tip 4 of the piercing element 1. A capillary structure is a structure that is dimensioned such that a body fluid sample therein is moved by capillary forces. It is also possible to have the capillary channel 3 only start at a distance from the tip 4 of the piercing element 1. The only aspect that is important in this connection is that, during puncture, the capillary channel 3 enters the body of a patient far enough for body fluid to travel into the capillary channel 3 and then be transported by the capillary forces.

The capillary channel 3 opens into a test region 5 containing detection reagents for determining an analyte concentration of a body fluid sample. The test region 5 can be provided, for example, with electrodes for electrochemical concentration determination, or it can enable photometric concentration determination by a concentration-dependent discoloration of the detection reagents. In the embodiment shown, the test region 5 is arranged on the carrier body 2, which is preferably made of synthetic material; however, other materials, such as metal, ceramic material or semiconductor material, are also possible.

Figure 3:
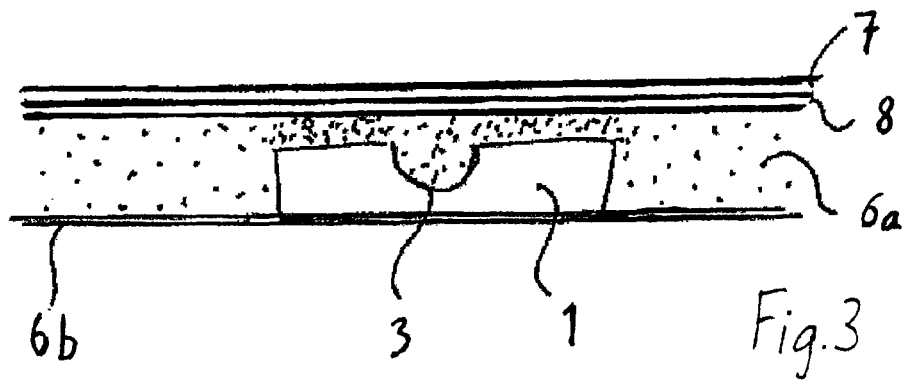
FIG. 3 shows a cross-section of a lancet along the intersecting line AA of FIG. 2.

FIG. 2 is a schematic illustration of a plurality of lancets comprising a sterile protection element 6 on a carrier strip 7, the protection element enclosing the tip 4 of the piercing element 1. FIG. 3 shows a sectional view along the intersecting line AA of FIG. 2. The section of the piercing element 1 enclosed by the sterile protection element 6a, 6b preferably has a length of more than 2 mm, for example 2 to 3 mm.

As is shown in FIG. 2, the piercing element 1 protrudes from the sterile protection element 6. The carrier body 2 and the test region 5 are disposed outside of the sterile protection element 6. The sterile protection element 6 is composed of two components 6a, 6b, which are shown schematically in FIG. 3. A first component 6a is a porous film, which covers a section of the upper side of the piercing element 1 and blocks the capillary channel 3 in the covered section by filling it in. At most a small gap of less than 10 μm remains between the sterile protection element and the piercing element 1 in the region of the filled-in capillary channel 3. The second component 6b is likewise a film in the embodiment shown, for example one made of paper, metal or—which is preferred—a polymer.

During production, the piercing element 1 is placed and pressed between the two films 6a, 6b. The first film 6a can be significantly compressed given the porosity thereof. During pressing, the first film 6a is significantly compressed by the piercing element 1 on both sides of the capillary channel 3. In the region of the capillary channel 3, the film 6a is compressed less significantly, or not at all, so that the capillary channel 3 is filled in by the film 6a. Pressing is preferably carried out at an elevated temperature, for example at more than 80° C., and more particularly at more than 100° C., so that the first film 6a can be deformed better and fill in the capillary channel 3.

After pressing, the two films 6a, 6b are joined to each other, preferably bonded, for example by gluing or welding.

The porous film 6a is preferably thicker than the piercing element 1, and more particularly the thickness of the film 6a is greater than the depth of the capillary channel 3. In the embodiment shown, the first film 6a is more than ten times, and preferably more than twenty times, as thick as the second film 6b. In the embodiment shown, the first film 6a has a thickness of more than 100 μm, for example 130 μm. The second film has a thickness of less than 10 μm, for example 6 μm.

The first film 6a can be, for example, a microporous membrane, as that which is distributed by the name of BTS 25 by the company Pall, Dreieich, Germany. The first film 6a can, for example, also be made of a foamed material, for example polystyrene. For this purpose, closed-cell foamed materials are preferable, but not absolutely essential. For example, the first film 6a can be covered with a sealing film on the side thereof facing away from the piercing element 1. The sealing film can be glued on or welded on. Such a sealing film preferably covers the entire upper side of the first film 6a. The sealing film may protrude laterally over the first film 6a and may be glued or welded to the second film 6b.

Polymer materials, which are easy to deform so as to fill in a section of the capillary structure as completely as possible, are the preferred material for the first component 6a of the sterile protection element. Moreover, it should be possible to remove the material as easily as possible from the capillary structure, and the material should not impair hydrophilic properties of the capillary structure to the extent possible.

After attaching the sterile protection element 6a, 6b, the piercing element 1 is sterilized by the effects of radiation, for example by gamma radiation. An irradiation dose of 25 kGray is generally sufficient. The sterilized piercing element 1 can then be handled without difficulty, because the parts entering the body of a patient during a puncture are protected by the sterile protection element 6a, 6b. The sterilized piercing element 1 is fastened to the carrier body 2, which carries a test region 5 containing detection reagents for determining an analyte concentration of a body fluid sample. The piercing element 1 can, for example, be glued to the carrier body 2 and/or inserted in a matching recess of the carrier body 2.

A film 8 is glued onto the surface of the first film 6a facing away from the piercing element 1, and preferably also onto the carrier body 2. The film 8 is preferably a double-sided adhesive tape, by which the lancet is then glued onto a carrier strip 7. To this end, it is not necessary for the film 8 to cover the entire surface of the porous film 6a or of the carrier body 2. It suffices if the film 8 covers a part of the surface of the carrier body 2 or of the porous film 6a.

FIG. 4 shows a side view of a lancet comprising the sterile protection element 6a, 6b and an adhesive film 8. To remove the sterile protection element, the carrier strip 7 can be bent, as is shown schematically in FIG. 5. By bending the carrier strip 7, the sterile protection element 6a, 6b folds away from the piercing element 1. In the process, the piercing element 1 breaks through the second film 6b, so that this film is folded away together with the first film 6a. Details regarding a handheld unit comprising a device for bending a carrier strip are described in International Publication No. WO 2008/083844 A1, Konya, published Jul. 17, 2008, for example (see also U.S. Patent Application Publication No. US 2009/0287116, Konya, published Nov. 19, 2009).

The carrier strip 7 is preferably a polymer film, the thickness of which is greater than the thickness of the second film 6b of the sterile protection element, for example it is thicker by at least half, and more particularly it is at least twice as thick. The carrier strip 7 can be, for example, a polyester film and have a thickness of 12 μm, for example.

REFERENCE NUMERALS

1 Piercing element
2 Carrier body
3 Capillary channel
4 Tip of the piercing element
5 Test region
6 Sterile protection element
6a First component of the sterile protection element
6b Second component of the sterile protection element
7 Carrier strip
8 Adhesive film

What is claimed is:

1. A lancet, comprising:
   a piercing element for puncturing the skin of a patient;
   a test region containing detection reagents for determining an analyte concentration of a body fluid sample;
   a capillary channel arranged in the piercing element for transporting a body fluid sample to the test region, wherein the capillary channel is a groove or a continuous slot; and
   a sterile protection element, which encloses the tip of the piercing element, the sterile protection element comprising a first component covering a section of an upper side of the piercing element and filling in the capillary channel in the covered section, and a second component covering a section of an underside of the piercing element; wherein the capillary channel is blocked in a section surrounded by the sterile protection element.

2. The lancet according to claim 1, wherein the capillary channel is blocked by the sterile protection element filling in the capillary channel at least over a part of the length.

3. The lancet according to claim 2, further comprising a carrier body fastened to the piercing element, wherein the carrier body protrudes from the sterile protection element.

4. The lancet according to claim 3, further comprising a film glued to both:
   (1) the side the first component facing away from the piercing element; and (2) a part of the carrier body that protrudes from the sterile protection element.

5. The lancet according to claim 1, wherein at least one of the two components is a film.

6. The lancet according to claim 1, wherein the first component is porous.

7. The lancet according to claim 6, wherein the first component is a polymer foam.

8. The lancet according to claim 1, wherein a film is glued to the side the first component facing away from the piercing element.

9. The lancet according to claim 8, further comprising a carrier body fastened to the piercing element, wherein the film glued to the first component is also glued to a part of the carrier body that protrudes from the sterile protection element.

10. The lancet according to claim 1, wherein the first component is thicker than the second component.

11. The lancet according to claim 10, wherein the first component is at least ten times as thick as the second component.

12. The lancet according to claim 1, wherein the piercing element is fastened to a carrier body, which carries the test region.

13. A carrier strip comprising a plurality of lancets according to claim 1, arranged thereon.

* * * * *